United States Patent [19]

Avoy

[11] Patent Number: 4,902,281
[45] Date of Patent: Feb. 20, 1990

[54] FIBRINOGEN DISPENSING KIT

[75] Inventor: Donald R. Avoy, Los Gatos, Calif.

[73] Assignee: Corus Medical Corporation, Costa Mesa, Calif.

[21] Appl. No.: 232,915

[22] Filed: Aug. 16, 1988

[51] Int. Cl.⁴ .............................................. A61M 5/00
[52] U.S. Cl. ...................... 604/191; 604/88; 604/201; 222/82; 222/137; 222/255; 239/304; 239/333
[58] Field of Search .......... 604/88, 148, 191, 200–201, 604/411–414; 222/82, 135, 137, 255; 239/304, 307, 309, 333

[56] References Cited

U.S. PATENT DOCUMENTS

| | | | |
|---|---|---|---|
| 2,941,696 | 6/1960 | Homm | 222/136 |
| 3,045,925 | 7/1962 | Giangualano | 239/306 |
| 3,236,418 | 2/1966 | Dalle et al. | 222/135 |
| 3,236,457 | 2/1966 | Kennedy et al. | 239/304 |
| 3,269,389 | 8/1966 | Meurer et al. | 128/198 |
| 3,405,706 | 10/1968 | Cinqualbre | 604/191 X |
| 3,604,410 | 9/1971 | Whitacre | 604/191 X |
| 3,714,943 | 2/1973 | Yanof et al. | 604/191 X |
| 3,760,986 | 9/1973 | Castner et al. | 222/255 X |
| 3,767,085 | 10/1973 | Cannon et al. | 222/82 |
| 3,828,980 | 8/1974 | Creighton et al. | 222/137 |
| 4,040,420 | 8/1977 | Speer | 128/218 |
| 4,260,077 | 4/1981 | Schroeder | 222/137 |
| 4,359,049 | 11/1982 | Redl et al. | 128/218 |
| 4,673,395 | 6/1987 | Phillips | 604/191 |
| 4,674,658 | 6/1987 | Van Brocklin | 222/137 |
| 4,697,622 | 10/1987 | Switft et al. | 604/407 X |
| 4,826,048 | 5/1989 | Skorka et al. | 222/137 |

FOREIGN PATENT DOCUMENTS 1232370 4/1960 France ................................ 239/309

OTHER PUBLICATIONS

Parke–Davis Thrombin, U.S. Patent Thrombostat Fact Sheet (Apr. 1986).
Calmar, Inc., TS–800 Fact Sheet.

Primary Examiner—Dalton L. Truluck
Attorney, Agent, or Firm—Knobbe, Martens, Olson & Bear

[57] ABSTRACT

Disclosed is a dispenser for separately dispensing each of two biological fluids contained therein for intermixing at a site outside of the dispenser to produce hemostasis or a tissue adhesive. The dispenser is compact, contains internal reservoirs of the two bioloical fluids, and is designed for efficient reloading with filled nonsterile containers without compromising the integrity of the sterile field. The dispenser is capable of dispensing the biological fluids, such as fibrinogen and thrombin, at either a focused point of in an aerosol mist. In addition, spray elements are disclosed for uniformly distributing the two biological fluids along either the interior surface or the exterior surface of an implantable vascular graft.

14 Claims, 3 Drawing Sheets

FIBRINOGEN DISPENSING KIT

BACKGROUND OF THE INVENTION

The in vivo mechanism for the clotting of blood requires conversion of the soluble protein fibrinogen into the insoluble protein fibrim in a reaction catalyzed by the enzyme thrombin. Thrombin is the activated form of prothrombin, a globulin circulating in the plasma. The conversion of prothrombin to thrombin requires a number of reactions involving the interaction of blood fractions having thermoplastic activity, including Stewart-Prower factor, Factor V, Factor VII and calcium. Several additional substances having thromboplastic activity have been identified, and are generally referred to by the genus thromboplastin.

Under the influence of thrombin, which is actually a proteolytic enzyme, and other blood factors, the blood protein fibrinogen loses several polypeptide chains to form fibrin. The fibrin then undergoes a polymerization to produce fibrin polymers which contribute to the physical properties of the clot.

The thrombin catalyzed polymerization of fibrinogen into fibrin is reproducible in vitro. For example, a system composed of purified fibrinogen, thrombin and added calcium produces the so-called Fibrin S polymer by spontaneous reversible polymerization. Polymerization is said to be reversible, due to the solubility of the Fibrin S polymer in dilute (0.03%) HCl.

However, an acid insoluble polymer of Fibrin I (insoluble fibrin) can be formed in vitro for example by addition of small amounts of serum to the in vitro system.

The serum contains a factor responsible for inhibition of the reversible polymerization of fibrin. This stabilizing factor in serum which enters the clotting sequence after fibrin has been formed, known as the Laki-Lorand factor (LLF) or fibrin stabilizing factor (FSF), is known to exhibit a useful stabilizing effect on the vitro polymerization of fibrinogen. Under the nomenclature proposed by the International Committee for the Standardization of the Nomenclature of Blood Clotting Factors, LLF is designated Factor XIII.

Thus, it is known that purified thrombin and fibrinogen, together with a variety of known adjuvants, can be combined in vitro to produce a polymer having great potential benefit, both as a hemostatic agent and as a tissue adhesive. Because of the rapid polymerization upon intimate interaction of fibrinogen and thrombin, it is important to maintain these two blood proteins separate until the application site. Previously, these materials have been delivered by devices such as a dual syringe apparatus which makes it possible to deliver the fluids for mixture at a small point.

One apparatus for applying a fibrinogen-based tissue adhesive is disclosed in U.S. Pat. No. 4,359,049 to Redl, et al. Redl discloses a complicated mechanism in which two standardized one-way syringes are held in a support having a common actuating means guided along a rod. Each of the delivery ends of the syringes is inserted into a collection manifold for delivery of the two components for mixing and delivery optimally through a mixing needle. However, it is often desirable or necessary to cover a broad area of a wound, either to stop bleeding, to fix tissue or to prevent infection.

Notwithstanding the contribution of Redl, there remains a need for a fibrinogen dispensing kit which is inexpensive, suitable for entry into the sterile field, and adaptable for convenient recharging of the fibrinogen or thrombin from a single source, as may be required during prolonged surgery or other procedure. In addition, the dispensing kit is advantageously capable of delivering the two blood proteins either at a focused point of delivery or as an aerosol mist for covering a region of tissue.

SUMMARY OF THE INVENTION

There has been provided in accordance with one aspect of the present invention a dispenser for separately dispensing each of two biological fluids contained therein, for intermixing at a remote site to produce hemostasis or a tissue adhesive, depending upon the application. The dispenser comprises a housing, having a first and a second pump therein. A first hollow aspirating needle in the housing is in fluid communication with the first pump, and a second hollow aspirating needle is in fluid communication with the second pump. The first and second needles extend within the housing into a chamber adapted for removably receiving a first and a second reservoir of biological fluids to be dispensed.

In a preferred embodiment, each of the first and second aspirating needles terminates in a sharp point, for piercing a septum on the reservoir of biological fluid. Preferably, one or both of the reservoirs comprise a standard vacuum bottle having a piercable, resealable septum as a closure member. The dispenser further comprises a first and a second hollow vent needle in the housing, extending into the chamber substantially parallel to the first and second aspirating needles, respectively, for communicating with the interior of the reservoirs.

In one embodiment of the present invention, the housing is further provided with a common actuator for simultaneously actuating each of the first and second pumps. The actuator is independently removably linked to each pump, to permit partial disengagement thereof for independent operation of the pumps. A cover is provided on the housing, for enclosing the chamber for receiving the reservoirs of biological fluid. The cover may be pivotally attached to the housing, or may be entirely removable from the housing. The cover comprises a cavity adapted to receive at least one of the reservoirs so that the cover may be loaded with the reservoirs and then installed as a unit into the housing.

In accordance with another aspect of the present invention, there is provided an interface device for placing a vacuum bottle having a resealable septum thereon in valved fluid communication with a source of fluid. The interface comprises a housing having a flow channel therethrough, and a valve in the flow channel. A hollow needle is provided in communication with the flow channel on the first side of the valve, and a hollow cannulae is provided in communication with the channel on the second side of the valve. The needle is adapted for piercing the septum on a vacuum bottle.

In accordance with a further embodiment of the present invention, there is provided a radial spray head for dispensing each of a plurality of fluids onto the interior surface of a tubular sleeve, comprising a first spray element having an influent passageway in fluid communication with each of a plurality of effluent ducts disposed about the periphery of the first spray element, and a second spray element comprising a second influent duct in fluid communication with each of a plurality of effluent ducts disposed about the periphery of the second spray element. The effluent ducts are disposed about the exterior periphery of the first and second spray elements for directing a spray in a radially outward direction.

For dispensing fluids on the exterior surface of a tubular sleeve, the first and second spray elements are provided with a cylindrical passageway therethrough for receiving the tubular sleeve. Effluent ducts are disposed about the surface of the cylindrical passageway for directing fluid in a radially inward direction.

These and other features and advantages of the present invention will become apparent from the detailed description of preferred embodiments which follows, when take together with the attached drawings and claims.

of droplets of the two fluids close to or at the application site.

Optimally, actuator 42 is removably linked to each of pumps 44 and 46 so that the pumps may be individually operated at the option of the clinitian. In applications where hemostasis is sought, an actuator 42 or its functional equivalent will likely be preferred. However, it may be desirable in some circumstances to individually dispense the fluids, such as one on each opposing surface of an incision. This will delay the rapid polymerization until the two surfaces are brought into contact.

Figures 1, 2, 3, 4, 5:
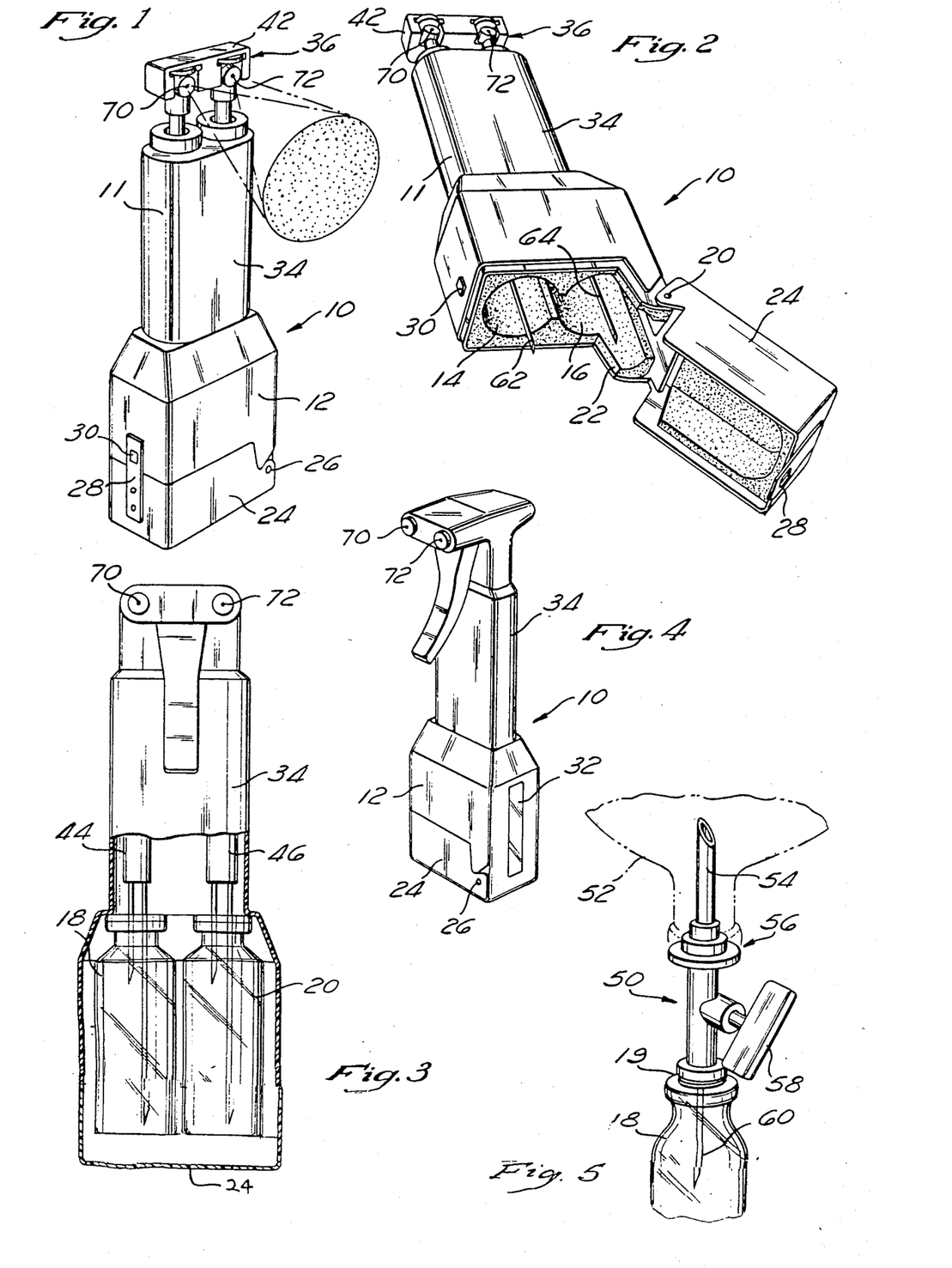
FIG. 1 is an elevational perspective view of a dispenser according to one embodiment of the present invention.
FIG. 2 is a perspective view of the embodiment illustrated in FIG. 1, showing the cover open and exposing the container receiving areas.
FIG. 3 is a partial sectional front elevational view of a dispenser according to a second embodiment of the present invention.
FIG. 4 is a perspective view of the embodiment illustrated in FIG. 3.
FIG. 5 is a perspective view of an interface for loading the containers used in the dispenser of the present invention.

Referring to FIG. 5, there is provided an interface device 50 adapted for placing a standard blood bag 52 or other container provided with a piercable septum 56 in fluid communication with a container 18 suitable for use in the dispensing kit 10 of the present invention. The interface 50 is provided at one end with a cannula 54 adapted for piercing the septum 56 contained on a standard blood bag 52. The interface 50 is further provided with a valve 58 which may be a stopcock, a pinch valve or any of a variety of known valving mechanisms for controlling the flow from the blood bag 52 into the container 18. The interface 50 is further provided with a hollow needle 60 in fluid communication by way of valve 58 with cannula 54, and adapted for piercing the resealable septum of a standard Vacutainer ® or other vacuum bottle.

Evacuated sterile container 18 is typically provided with a piercable septum 19 for maintaining a vacuum therein. In use, the interface 50 will be placed in fluid communication with the fluid contents of blood bag 52 by way of cannula 54. With valve 58 in the closed position, needle 60 on interface 50 is inserted through resealable septum 19 on container 18. When valve 58 is open, fluid contents from blood bag 52 are drawn into the interior of container 18 due to the vacuum contained therein. When sufficient contents have been transferred into the container 18, valve 58 is closed and container 18 is removed from needle 60. Container 18 is then ready for insertion into one of container receiving areas 14, 16 on dispensing kit 10.

As container 18 is inserted into one of container receiving areas 14 or 16, the resealable septum 19 is first pierced by one of aspirating needles 62, 64. Aspirating needles 62, 64 are in fluid communication by way of pumps 44, 46 with effluent ducts 70, 72 on spray head 36. Aspirating needles 62, 64 are disposed such that when containers 18, 20 are fully inserted into the container receiving areas 14, 16, the needles will reach substantially to the bottom of the interior of the containers.

As the container 18 is further inserted into the container receiving area 14, resealable septum 19 will be pierced by a second vent needle 66. A vent needle 66, 68 is desirable to equalize pressure inside containers 18, 20, as fluid contents are drawn out through needle 62 or 64.

As an alternative to Vacutainer ® containers 18 and 20, nonvacuum bottles could also be used in the dispensing kit 10 of the present invention. Sample bottles can be used which have a threaded neck such as to receive a cap, or which are provided with a luer or other mechanical interfit connection. The innermost extent of container receiving areas 14, 16 would be provided with a corresponding structure for engaging the luer or other interfit structure on the sample bottle. In this embodiment, it would be unnecessary for the aspirating needles 62, 64 to have sharpened ends.

Figures 16, 17:
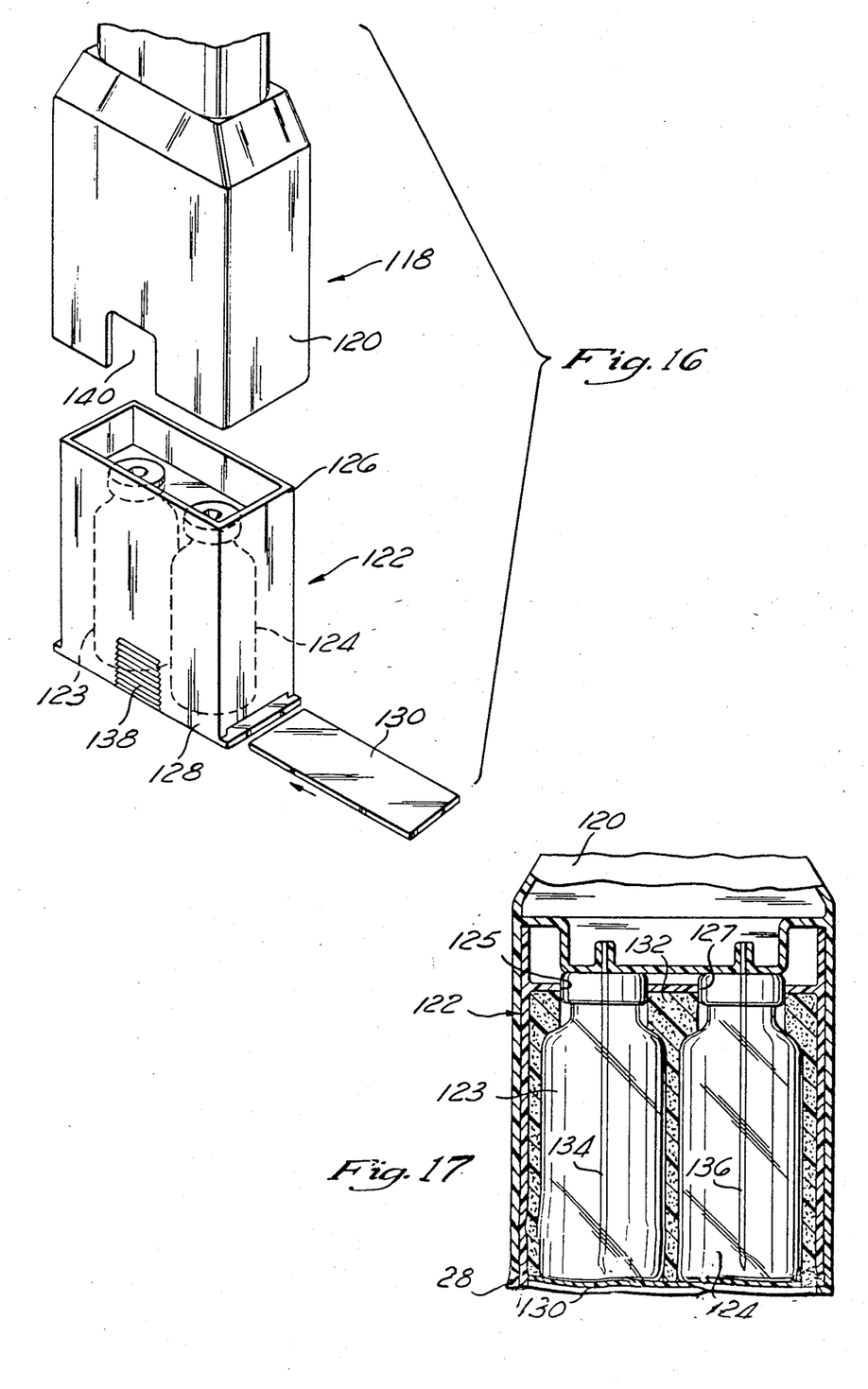

In accordance with a further embodiment of the present invention, there is provided a modified dispensing kit adapted to receive the containers of fibrinogen and thrombin within a removable cassette. Referring to FIG. 16, there is illustrated in exploded form a dispenser 118 and cassette 122, in accordance with the present invention. As illustrated therein, housing 120 of dispenser 118 is adapted to slidably receive the upper end 126 of cassette 122. Cassette 122 may be produced in accordance with any of a variety of known methods, such as thermoplastic forming techniques, and optimally comprises acrylic, styrene or other rigid thermoplastic material. Cassette 122 may conveniently be formed in the same manner and of the same materials as the dispenser 10 described previously. In addition, cassette 122 is provided with insulation 132 for surrounding containers 123 and 124 as has been discussed.

The lower end 128 of cassette 122 is provided with a door 130 for providing access to the interior of the cassette 122. Door 130 is illustrated as a slidable panel, however, any of a variety of doors may be used as will be appreciated by one of skill in the art. Opening door 130 permits access to the interior of cassette 122 for insertion of containers 123 and 124, illustrated in phantom in FIG. 16. The upper end 126 of cassette 122 is provided with openings 125 and 127 to expose the containers 123 and 124 for providing fluid communication with the pumps, as will become apparent.

Cassette 122 is further provided with a pair of opposing surfaces 138 for providing friction so that the cassette may be conveniently gripped, such as between the thumb and forefinger, and inserted or withdrawn with respect to housing 120. Housing 120 is provided with a corresponding pair of openings 140 which expose the surfaces 138 when the cassette 122 is fully inserted into housing 120. Any of a variety of additional structures for facilitating removal of cassette 122 may be used, as will be apparent to one of skill in the art.

Referring to FIG. 17, there is disclosed a partial elevational cross-sectional view of a cassette embodiment of the dispenser of the present invention, illustrating the cassette 122 inserted into the housing 120. As seen therein, cassette 122 is dimensioned so that its exterior wall permits a snug fit with the interior of housing 120 for retaining the cassette therein. In addition, static friction will exist between each of needles 134 and 136, and the piercable septums on containers 123 and 124, respectively, which are arranged in a similar manner as the needles and septums or other closures previously discussed. Any of a variety of structures well known to one of skill in the art may additionally be utilized for retaining cassette 122, such as releasably interlocking ridges and grooves on the interior surface of housing 120 and exterior surface of cassette 122 as will be appreciated by one of skill in the art.

As cassette 122 is inserted into housing 120, needles 134 and 136 pierce the corresponding closure members on containers 123 and 124, as has been previously discussed. For simplification purposes, vent needles, which have been discussed in connection with previous figures, have been deleted from FIG. 17.

The removable cassette embodiment accrues the important advantage in the operating room of providing a convenient bridge across the boundary of the sterile field. The dispensing kit 118, including the exterior of cassette 122 must be maintained sterile throughout a procedure in the operating room. However, the exterior of the containers themselves will not be sterile. The embodiment of FIGS. 16 and 17 enables the sterile nurse or physician to hold cassette 27 while the circulating nurse inserts filled containers 123 and 124 into cassette 122. The cassette 122 can then be fit onto housing 120 without compromising the integrity of the sterile field.

In operation, a nurse or other attendant will typically reconstitute lyophilized thrombin from bovine or other source by mixing with water or isotonic saline diluents in accordance with known techniques. Lyophilized thrombin may be commercially obtained, for example, from the Parke-Davis division of Warner-Lambert Co. (Morris Plains, NJ) which markets bovine thrombin in 5, 10 and 20 ml vials under the name Thrombostate ®.

The reconstituted thrombin is then warmed to and maintained at approximately 37° celsius in the container 18 or 20 for installation in the dispenser 10. The fibrinogen is warmed from its refrigerated storage temperature to approximately 37° celsius and loaded into a blood bag if not so stored, or other suitable storage apparatus to be suspended from an IV pole in a location convenient to the operating table or other procedure site.

An interface device 50 is provided for the fibrinogen bag, and a fibrinogen container 18 is then filled as previously described and inserted into the dispensing kit 10 along with a bottle of reconstituted thrombin. Fibrinogen is typically available on an autologous basis or from a single donor source of plasma, which will be fractionated by a blood bank to produce a fibrinogen concentrate. Although fibrinogen extracts from multiple sources are commercially available in some countries, they are not yet in the United States due to certain prescreening difficulties known to those of skill in the art.

In the course of the surgical procedure, if additional fibrinogen and thrombin are necessary, additional vacuum bottles or other container 18 can be conveniently loaded from blood bag 52 or reconstituted and inserted into the dispensing kit 10 as needed. The ability to refill the dispensing kit 10 from a single source of each of the fibrinogen and thrombin accrues important advantages, particularly under circumstances when single source or autologous fibrinogen is being used.

As previously discussed, the fibrin polymer formed from the interaction of fibrinogen and thrombin may be advantageously applied in a variety of clinical situations. In addition to use as a tissue adhesive either during surgery or as a temporary emergency measure, and to the use of the fibrin polymer as a hemostatic agent, another important application relates to the implantation of vascular prostheses. Synthetic tubular grafts available for use in vascular surgery have been surgically implanted in hundreds of thousands of individuals over the course of the last decade. One such graft is comprised of rapidly stretched highly crystalline polytetrafluoroethylene, and is currently marketed by W. L. Gore & Associates, Inc.

One difficulty associated with the implantation of woven or stretched vascular prostheses is the occurrence of leakage when initially sutured into the vascular system. Leakage is an inherent result of the desirability of having a porous structure to permit interweaving of the tissue, and can particularly be a problem if the patient has been anticoagulated through the use of such agents as heparin or other anticoagulants utilized in the operating room. Hence, it is advantageous to be able to pretreat the porous vascular graft prior to implantation to prevent leakage therethrough during the period of time required for the tissue growth to render the implant fluid-tight.

Figures 6, 7:
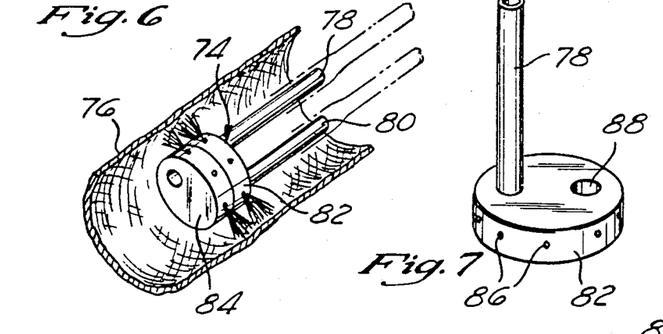
FIG. 6 is a perspective view of a dual fluid radial dispenser according to the present invention, for dispensing fluid on the interior of a tubular vascular graft.
FIG. 7 is a perspective view of a single element from the radial dispenser shown in FIG. 6.

Thus, there is additionally provided in accordance with the present invention a radial spray head 74 for uniformly dispensing each of two solutions containing fibrinogen and thrombin, respectively, onto the interior surface of a tubular sleeve 76, as illustrated in FIG. 6. The tubular sleeve 76, illustrated in a cutaway view, may be any of a variety of commercially available vascular prostheses as previously discussed. The radial spray head 74 comprises a first spray element 82 and a second spray element 84 in fluid communication by way of a first influent passage 78 and a second influent passage 80, respectively, with a source of the fibrinogen and thrombin containing solutions. The radial spray head 74 may be conveniently connected by way of a delivery conduit 110, such as that illustrated in FIG. 15, to the dispensing kit 10 of the present invention.

The radial spray head 74 is comprised of two spray elements 82, 84, which may be conveniently produced such as by a molding process to be identical to one another in configuration. For example, in FIG. 7 there is illustrated a single spray element 82 which arbitrarily has been designated as the first spray element 82 corresponding to FIG. 6. In the spray element 82, the influent passage 78 is in fluid communication with a plurality of effluent ducts 86 directed radially outwardly around the periphery of the spray element 82. Although the spray element 82 is illustrated as being substantially cylindrical in configuration, that is merely a preferred configuration due to the likelihood that most tubular vascular grafts will be of substantially circular cross section. However, for particular applications, it may be desirable to have a radial spray head 74 having a non-cylindrical configuration depending upon the particular application.

Figure 8:
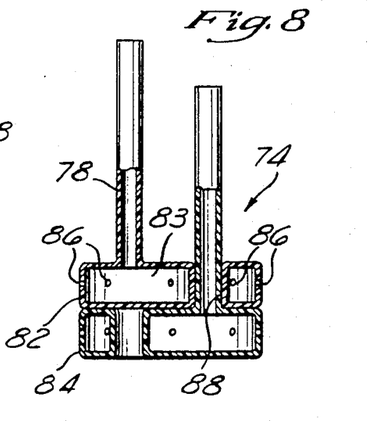
FIG. 8 is a partial cross-sectional view of the dispenser shown in FIG. 6.

As illustrated in each of FIGS. 6-8, the spray elements 82 and 84 are each provided with a passageway 88 which performs no function in the distal spray element 84. In the proximal spray element 82, however, the passageway 88 permits stacking of the proximal and distal spray elements on top of one another by receiving the second influent passage 80 therethrough. This design is selected for manufacturing convenience and, of course, other configurations could readily be devised.

Referring to the partial cross-sectional view in FIG. 8, it is seen that each of the influent passageways is respectively in fluid communication with the corresponding spray element. In a relatively large embodiment of the spray head 74, which may be desirable, for example, in applications utilizing larger arterial grafts, there may exist an undesirable dead space within the interior chamber 83 of element 82 so that a substantial quantity of fluid must be introduced into the spray element 82 before that element will express fluid uniformly around its periphery. Thus, it may be desirable to reduce the interior volume of the chamber 83. This can be accomplished, for example, by molding the spray element 82 such that only a relatively small annular flow passageway remains around the periphery of the spray element 82, for providing fluid communication between influent passage 78 and each of the effluent ducts 80.

The size and spacing of the effluent ducts 86 illustrated in FIGS. 6-8 is for illustrative purposes only, and a wide variety of duct patterns and spacings could be utilized in accomplishing the objectives of the present invention. In an alternate embodiment, spray element 82 could be comprised of a top and a bottom half which form therebetween a single annular effluent duct extending radially all the way around the periphery of the spray element 82. The efficacy of a single annular groove embodiment would be dependent upon manufacturing tolerances, and the use of a plurality of drilled or molded effluent ducts 86 may therefore be superior.

Figures 11, 12, 13, 14, 15:
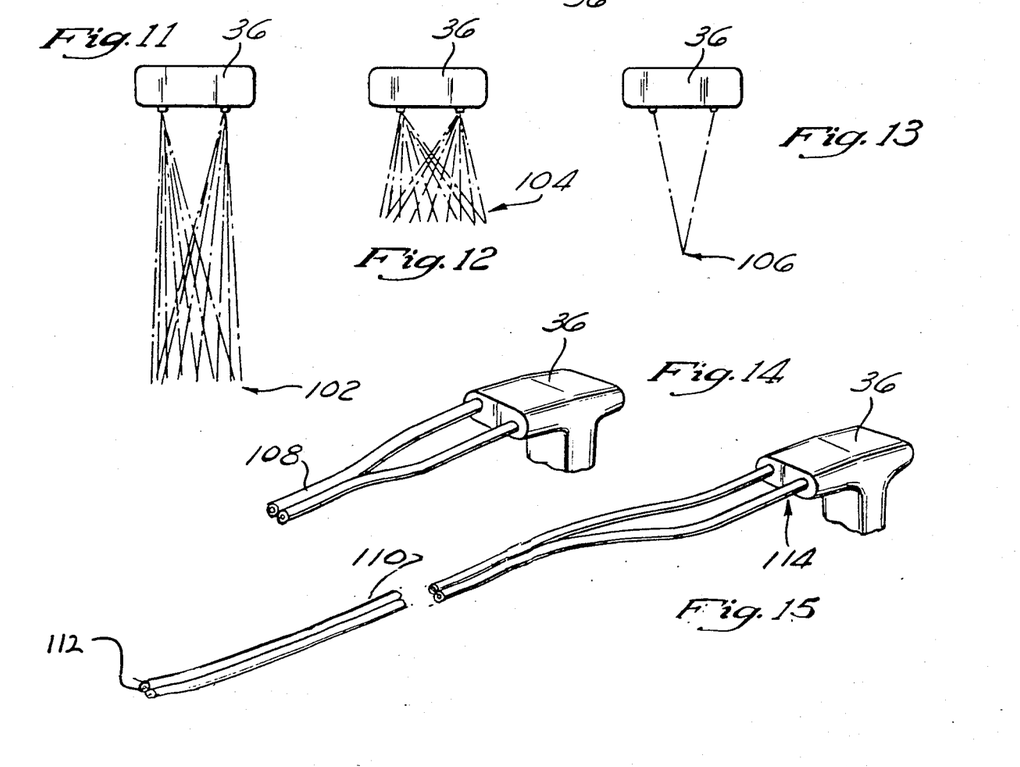
FIG. 11 illustrates a spray pattern of a dispensing head according to the present invention, wherein intermixing occurs at a first distance from the spray head.
FIG. 12 is a dispenser head according to the present invention, wherein intermixing occurs at a second distance from the spray head.
FIG. 13 illustrates a third embodiment of the spray head, wherein intermixing occurs at a focused point.
FIG. 14 illustrates a rigid attachment for conducting blood proteins to a remote location.
FIG. 15 illustrates an elongate flexible attachment for conducting blood proteins from the spray head of the present invention to a remote location.

In use, the radial spray head 74 may be placed in fluid communication with the dispensing kit 10 or other source of fluids by way of a delivery conduit 110 such as that illustrated in FIG. 15. Prior to implantation of the vascular graft, the radial spray head 74 may then be positioned within the vascular graft and drawn therethrough as fluid is expressed from the dispensing kit 10. In this manner, uniform quantities of the fibrinogen and thrombin solutions will be dispersed along the interior surface of the tubular sleeve 76, thereby forming a fluid-impermeable layer thereon.

Figures 9, 10:
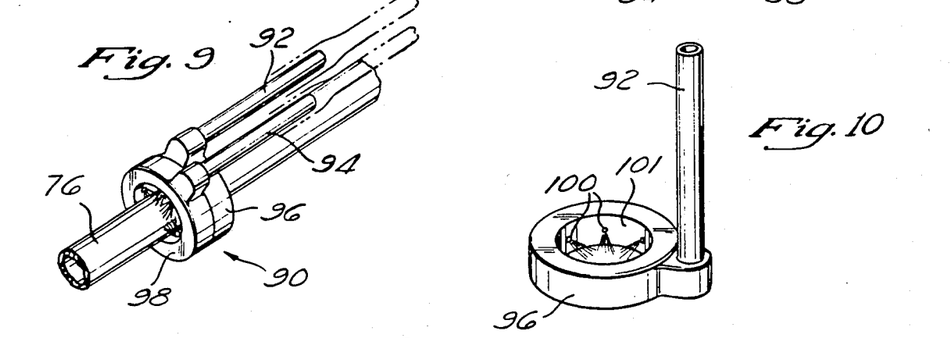
FIG. 9 is a radial dispenser for dispensing fluids on the exterior surface of a tubular sleeve.
FIG. 10 is a perspective view of a single fluid dispensing element from the dispenser shown in FIG. 9.

As an alternative to or in addition to the interior spray head 74, there has further been provided in accordance with the present invention a spray element 90 for uniformly dispensing a plurality of fluids along the exterior of a tubular sleeve 76 (see FIG. 9). The radial spray head 90 comprises a first spray element 96 in communication with a source of fluid by means of first influent passage 92, and a second spray element 98 in communication with a source of fluid by way of second influent passage 94. Influent passages 92, 94 may be similarly placed in fluid communication with a source of fluids such as dispensing kit 10 by way of a delivery conduit 110. The first and second spray elements 96, 98 may be identical in configuration, and a single spray element 96 is illustrated in FIG. 10. Referring to FIG. 10, the first influent passage 92 is in fluid communication by way of an annular chamber (not illustrated) in spray element 96 with a plurality of effluent ports 100 dispersed radially around the interior of the torus-shaped element 96. The cylindrical opening through spray head 96 has a diameter to facilitate insertion of tubular sleeve 76 therethrough. As with the spacing of the effluent ducts 86 on the spray head 74 illustrated in FIG. 6, the frequency and configuration of the effluent ports 100 can vary considerably, however, it is contemplated that about ten or more effluent ports per inch of arc length along the interior cylindrical surface 101 of spray element 96 will be used.

Each element 96, 98 of the spray head 90 is illustrated with the influent passage disposed at a perpendicular to the plane of the spray element. This configuration may conveniently be accomplished by displacing the axis of effluent passage 92 radially outwardly from the exterior diameter of spray element 96. In this manner, identical spray elements can be stacked one on top of another without interference from influent passageways.

Of course, the configuration can be modified in a variety of ways and still accrue the advantages of the present invention. For example, the axis of effluent passageway 92 could coincide with the annular chamber within spray element 96. In that embodiment, the spray element 96 would need to be provided with an opening conceptually equivalent to passageway 88, illustrated in FIGS. 6-8, to permit stacking of the spray heads 96, 98. Alternatively, it may be desirable for the influent passageways 92, 94 to extend radially outwardly from the spray elements 96, 98 such that they extend at a perpendicular from the tubular sleeve 76 when in use. In this embodiment, the influent passageways could be integral with a handle for convenient operation of the spray head.

Use of the interior spray head 74 and exterior spray head 90 is advantageously accomplished through the use of a delivery conduit 110, illustrated in FIG. 15. Delivery conduit 110 is a dual channel conduit comprised of a flexible, resilient material which is substantially inert in the presence of the fibrinogen and thrombin solutions to be conducted therethrough. Distal end 112 can be secured in fluid communication with a spray head, such as that illustrated in FIGS. 6 or 9, by friction fit with the influent passageways thereof. Alternatively, any of a variety of other known connection means can be employed.

Similarly, proximal end 114 of delivery conduit 110 is advantageously dimensioned to enable a friction fit to provide fluid communication with ducts 70 and 72 on spray head 36. Alternatively, proximal end 114 and spray head 36 can be provided with positive interlocking structures such as a luer connection or other known lock.

The delivery conduit 110 can be provided in a variety of different lengths, depending upon the intended use. Typically, vascular grafts for human implantation may be anywhere from about 10 cm to as long as 30 cm in length, or longer, and conduits of that length or less are currently envisioned. In another application of the present invention, a flexible delivery conduit 110 is provided having sufficient length to extend through the working channel in any of a variety of instruments such as an endoscope, arthroscope, or gastroscope which permits visualization at a remote site. This structure permits visualization and release of the fibrinogen and thrombin solutions at a remote spot in any of a variety of body cavities where hemostasis or an adhesive may be desired, such as a treatment for ulcerations in the stomach or gastrointestinal tract, or as a postoperative measure following such procedures as a tonsillectomy, adenoidectomy or more remote surgery. In a further embodiment, delivery conduit 108 (FIG. 14) is typically shorter than conduit 110, and is rigid for precisely controlled delivery at a more accessible specified point.

Although this invention has been described in terms of certain preferred embodiments, other embodiments that are apparent to those of ordinary skill in the art are also within the scope of this invention. Accordingly, the scope of the invention is intended to be defined only by reference to the appended claims.

I claim:

1. A dispenser for separately dispensing each of two biological fluids contained therein for intermixing at a remote site to produce hemostasis or a tissue adhesive, comprising:

a housing having a dispenser head thereon for separately dispensing each of two fluids;
a first and second pump in the housing;
a first hollow aspirating needle in the housing, in fluid communication with the first pump;
a second hollow aspirating needle in the housing, in fluid communication with the second pump; and
a chamber in the housing for removably receiving a first and a second reservoir of biological fluids to be dispensed,
wherein each of the first and second aspirating needles extends into the chamber for providing fluid communication with each of the first and second reservoirs of biological fluid, respectively, so that activation of the first and second pump produces a flow of biological fluid from the first and second reservoirs through the first and second aspirating needles and out of the dispenser head for intermixing at a remote site outside of the dispenser.

2. A dispenser as in claim 1, wherein each of the first and second aspirating needles terminates in a sharp point, for piercing a septum on the reservoir of biological fluid.

3. A dispenser as in claim 1, further comprising a first and second hollow vent needles in the housing, extending into the chamber substantially parallel to the first and second aspirating needles, respectively, for communicating with the interior of the reservoirs.

4. A dispenser as in claim 1, further comprising a common actuator for simultaneously actuating each of said first and second pumps.

5. A dispenser as in claim 4, wherein the actuator is removable secured to the pumps to permit removal thereof for independent operation of the pumps.

6. A dispenser as in claim 1, further comprising a cover on the housing, for enclosing the chamber to prevent accidental removal of the first and second reservoirs of biological fluids.

7. A dispenser as in claim 6, wherein the cover is pivotally attached to the housing.

8. A dispenser as in claim 7, wherein the cover further comprises a latch for securing the cover in the closed position.

9. A dispenser as in claim 1, further comprising a layer of thermal insulating material disposed on the inside surface of the chamber.

10. A dispenser as in claim 1, further comprising a spray head having a first and a second effluent ducts, in fluid communication with the first and second pumps, respectively, for directing a first and second stream of biological fluid for intermingling at a target site.

11. A dispenser as in claim 10, wherein each of the first and second effluent ducts is adjustable from a first position for producing a steady stream of fluid, to a second position for producing an aerosol mist.

12. A dispenser as in claim 10, wherein the effluent ducts are adjustable from a first position wherein the effluent streams converge at a first distance from the spray head, to a second position wherein the effluent streams converge at a second distance from the spray head.

13. A dispenser as in claim 6, wherein the cover is removably secured to the housing, and the cover comprises a cavity adapted to receive at least one of the reservoirs so that the cover may be loaded with the reservoirs and then installed as a unit into the housing.

14. A dispenser for sepaqrately dispensing each of two biological fluids contained therein for intermixing at a site outside of the dispenser to produce hemostasis of a tissue adhesive, said dispenser adapted for removably receiving a cassette containing the biological fluids so that the dispenser may be reloaded by replacement of an exhausted cassette, comprising:

a dispenser housing having a chamber adapted for removably receiving a cassette;

a cassette removably disposed in the housing for holding a first and a second reservoir of biological fluids to be dispensed;

a first and a second pump in the housing a first hollow aspirating needle in the housing, in fluid communication with the first pump and extending into the chamber so that when a loaded cassette is positioned in the chamber the first hollow needle will provide a path of fluid communication between the first reservoir and the first pump; and a second hollow aspirating needle in the housing, in fluid communication with the second pump and extending into the chamber so that when a loaded cassette is positioned in the chamber the second hollow needle will provide a path of fluid communication between the second reservoir and the second pump, wherein the first and second pumps are placed in fluid communication with the first and second reservoirs, respectively, when the cassette is engaged with the dispenser housing, so that the first and second pump when activated, produce a flow of biological fluid from the first and second reservoirs through the first and second aspirating needles and out to the dispenser.

* * * * *

UNITED STATES PATENT AND TRADEMARK OFFICE
CERTIFICATE OF CORRECTION

PATENT NO. : 4,902,281
DATED : February 20, 1990
INVENTOR(S) : Donald R. Avoy

It is certified that error appears in the above-identified patent and that said Letters Patent is hereby corrected as shown below:

Column 1, line 12, change the words "having thermoplastic activity" to --having thromboplastic activity--

Column 1, line 39, change the words "the vitro" to --the in vitro--

Column 3, line 15, change the words "take together" to --taken together--

Column 5, line 41, change the words "dispensing kit 0!" to --dispensing kit 10--

Column 6, line 18, change the words "cassette !22" to --cassette 122--

Signed and Sealed this

Twenty-eighth Day of January, 1992

Attest:

HARRY F. MANBECK, JR.

*Attesting Officer*  *Commissioner of Patents and Trademarks*